(12) United States Patent
Samsoondar et al.

(10) Patent No.: US 6,353,471 B1
(45) Date of Patent: Mar. 5, 2002

(54) METHOD AND APPARATUS FOR NON-DESTRUCTIVE SCREENING OF SPECIMEN INTEGRITY

(75) Inventors: James Samsoondar, Cambridge (CA); Merrit Nyles Jacobs, Fairport, NY (US)

(73) Assignee: CME Telemetrix Inc., Waterloo (CA)

( * ) Notice: Subject to any disclaimer, the term of this patent is extended or adjusted under 35 U.S.C. 154(b) by 0 days.

(21) Appl. No.: 08/871,606

(22) Filed: Jun. 9, 1997

Related U.S. Application Data

(63) Continuation-in-part of application No. 08/541,390, filed on Oct. 10, 1995, now abandoned.

(51) Int. Cl.⁷ .............................................. G01N 33/48
(52) U.S. Cl. ...................................................... 356/40
(58) Field of Search ................................. 356/326, 328, 356/330–334, 434, 244, 246, 39–42; 422/63, 67, 82.05; 436/171–172

(56) References Cited

U.S. PATENT DOCUMENTS

| | | | |
|---|---|---|---|
| 3,702,736 A | * | 11/1972 | Coggeshall |
| 5,066,859 A | | 11/1991 | Karkar et al. |
| 5,288,646 A | | 2/1994 | Lundsgaard et al. |
| 5,291,884 A | | 3/1994 | Heinemann et al. |
| 5,351,685 A | | 10/1994 | Potratz |
| 5,353,790 A | | 10/1994 | Jacques et al. |
| 5,360,004 A | | 11/1994 | Purdy et al. |
| 5,366,903 A | | 11/1994 | Lundsgaard et al. |
| 5,734,468 A | | 3/1998 | McNeal |
| 5,846,492 A | * | 12/1998 | Jacobs et al. |

FOREIGN PATENT DOCUMENTS

| | | |
|---|---|---|
| CA | 2019511 | 9/1994 |

* cited by examiner

*Primary Examiner*—K. P. Hantis
(74) *Attorney, Agent, or Firm*—Katten, Muchin & Zavis

(57) ABSTRACT

A method and apparatus for providing a non-destructive pre-test screen of specimen integrity for a blood analyzer by measurement of absorbance or reflectance is provided. The method involves measurement of polychromatic light in the near infrared and adjacent visible region, which is either transmitted or reflected from a specimen as presented for measurement, and correlation of the measurement, on the basis of predetermined algorithms, to the quantity of a known substance contained in the sample. The apparatus employs a spectrophotometer which emits radiation which is split into a beam which passes to a sample and a reference beam, the beam returning from the sample and the reference beam are variably combined and further separated into various components by means of a grating and focused onto a linear array detector. A microprocessor receives output from the array detector and performs calculations of concentration(s) of the known substance(s). The invention provides quality assurance for state-of-the art blood analyzers and automated laboratories by pre-screening serum and plasma integrity, even where labels on the sample container would normally interfere with a quality assurance assessment, identifying samples not suitable for certain blood tests, or, if tests are conducted on specimens with compromised integrity, the pre-screening results will aid in the interpretation of the test results.

15 Claims, 12 Drawing Sheets

METHOD AND APPARATUS FOR NON-DESTRUCTIVE SCREENING OF SPECIMEN INTEGRITY

This application is a continuation-in-part of U.S. Ser. No. 08/541,390 filed Oct. 10, 1995, now ABN the contents of which are hereby incorporated by reference.

FIELD OF THE INVENTION

This invention relates to spectrophotometry and the spectrophotometric analysis of blood samples. In particular, this invention relates to a method and apparatus for providing a non-destructive pre-test screen of specimen integrity for a blood analyzer by measurement of absorbance or reflectance.

BACKGROUND OF THE INVENTION

Clinical laboratory tests are routinely performed on the serum or plasma of whole blood. In a routine assay, red blood cells are separated from plasma by centrifugation, or red blood cells and various plasma proteins are separated from serum by clotting prior to centrifugation.

Haemoglobin (Hb), bilirubin (Bili) and light-scattering substances like lipid particles are typical substances which will interfere with, and affect spectrophotometric and other blood analytical measurements. Such substances are referred to as interferents. Elevated Bili can be due to disease states, and increased lipid particles in the blood, also known as hyperlipidemia, can be due to disease states and dietary conditions. Elevated Hb in the blood, hemoglobinemia, can be due to disease states and as a result of specimen handling. Clinical laboratories currently emphasize these three potential interferents as being of greatest concern with respect to affecting blood analysis. Biliverdin, (BV), a fourth potential interferent, is rarely mentioned.

BV is the precursor of Bili, and if Bili becomes oxidized, it will revert to BV. BV and Bili are two of a class of compounds referred to as bile pigments. BV is not normally present in serum, but regularly accompanies Bili in the serum of patients with carcinomatous obstruction of the bile duct, and is frequently found in the blood of patients with liver cirrhosis, and bile duct occlusion by gallstones.

Upon visual inspection, Bili gives a yellow or orange colour to serum and 10 plasma and is considered to be the major bile pigment in serum or plasma. Bili is sometimes described as a greenish/yellow pigment (Guyton, A. C. and Hall, J. E., Textbook of Medical Physiology, 1996, page 886). However, it is likely BV, rather than Bili, that is responsible for the greenish colour. In fact, these specimens may, nevertheless, have acceptable levels of Bili. A yellow colour chart is available for visual grading of Bili levels in serum or plasma, but there is no known colour chart for green bile pigment or BV. Visual inspection may still provide any opportunity for rejection of green specimens, however, for automated systems, no method exists for screening serum or plasma specimens for increased blood levels of BV, also known as hyperbiliverdinemia.

Many tests conducted on plasma or serum samples employ a series of reactions which terminate after the generation of chromophores which facilitate detection by spectrophotometric measurements at one or two wavelengths. Measurement of interfering substances prior to conducting such tests is important in providing meaningful and accurate test results. In fact if a sample is sufficiently contaminated with interferents, tests are normally not conducted as the results will not be reliable.

Specimen integrity is an essential part of quality assurance as it directly affects the accuracy of test results. The presence of interferents in a plasma or serum sample compromises specimen integrity.

Spectrophotometric measurement uses infrared (IR) or near infrared radiation (NIR) to assess the concentration of various constituents in a blood sample. Examples of photometric measurements using containers which hold a blood sample are disclosed in U.S. Pat. Nos. 5,291,884; 5,288,646; 5,066,859; and 5,366,903.

U.S. Pat. No. 5,366,903 discloses a sampling device which allows photometric quantitative determination of an analyte in whole blood. The device overcomes the problems of having blood cells in a blood sample by effectively "squeezing out" red blood cells and providing a small volume of sample, free of red blood cell material, from which particular analytes can be measured.

Other applications of photometric methodology include non-invasive determinations of analyte concentrations such as described in U.S. Pat. Nos. 5,360,004; 5,353,790; and 5,351,685. However none of these documents discloses a method of measuring interferents in the plasma or serum of a blood sample, in order to assess specimen integrity for further analysis.

Current methods used for detecting haemoglobinemia, bilirubinemia and lipemia or turbidity utilize visual inspection of the specimen with or without comparison to a coloured chart. It is to be understood that those practising in the field use the terms lipemia and turbidity interchangeably. This is so because lipemia is the major cause of turbidity in serum or plasma.

Visual inspection is sometimes employed on a retrospective basis where there is a disagreement between test results and clinical status of the patient in order to help explain such discrepancies.

A sample of plasma or serum is normally transferred from an original or primary tube or container to a secondary tube or container. These secondary tubes are amber coloured to protect photo sensitive constituents. The amber colouring makes visual inspection virtually impossible. On occasion, labels cover portions of the tube further restricting a full visual examination.

Pre-test screening of specimens by visual inspection is semi-quantitative at best, and highly subjective and may not provide sufficient quality assurance as required for some tests.

Furthermore, visual inspection of specimens is a time consuming, rate limiting process. Consequently, state-of-the-art blood analyzers in fully and semi-automated laboratories do not employ visual inspection of specimens.

Other methods to assess specimen integrity employ direct spectrophotometric measurement of a diluted sample in a special cuvette. However, such methods are not rapid enough for screening samples. In order to obtain a measurement of the sample of the plasma or serum, primary specimen tubes, or containers, must be uncapped, a direct sample of the specimen taken and diluted prior to measurement. Both of these steps are time consuming and require specialized and/or disposable cuvettes.

SUMMARY OF THE INVENTION

It is desirable to provide an apparatus and a method whereby specimen integrity is rapidly and accurately assessed without disturbing the sample. The disadvantages of the prior art may be overcome by providing a rapid and accurate method and apparatus for monitoring blood specimen integrity before samples are presented for analysis.

In one aspect of the invention, spectral data is used in a novel way so as to determine if the specimen which is presented for such analysis in a primary container contains interferents and if so, to what extent.

In another aspect of the invention, there is provided an apparatus and a method for determining blood specimen integrity of a specimen contained in a primary container using a spectrophotometer to irradiate and measure radiation from the specimen.

In a further aspect of the invention, there is provided an apparatus and a method for determining blood specimen integrity, where a primary sample tube containing a specimen has a sample identification label on the exterior surface of the sample tube, by using a spectrophotometer to irradiate and measure radiation from the specimen.

In yet another aspect of the invention there is provided an apparatus and a method for determining blood specimen integrity of a specimen contained in a primary container where light is transmitted through the label, container and specimen.

In yet a further aspect of the invention, there is provided an apparatus and a method for determining blood specimen integrity of a specimen contained in a primary container, where the light is reflected from the backside of a label after penetrating the specimen and container through an unlabelled section of the container.

In another aspect of the invention, specimen integrity of a specimen contained in a primary container is assessed by measuring:

1. Haemoglobin concentration as an assessment of haemolysis;
2. Bilirubin concentration as an assessment of bilirubinemia;
3. Biliverdin concentration as an assessment of biliverdinemia; and
4. Equivalent intralipid concentration for the assessment of turbidity.

Bile pigments may be measured in accordance with the method and apparatus of the present invention. According to one aspect of the present invention, Hb concentration is determined by measurement of absorption of different wavelengths of light in serum or plasma specimens which are then compared with values obtained through calibration using reference measurements for haemoglobin in serum or plasma specimens. Bili and/or BV_concentration is determined by measurement of absorption of different wavelengths of light in serum or plasma specimens which are then compared with values obtained through calibration using reference measurements for Bili and/or BV in serum or plasma samples. Turbidity is determined by measurement of absorption of different wavelengths of light in serum or plasma specimens which are then compared with values obtained through calibration using serum samples spiked with known amounts of intralipid (IL). Intralipid is a fat emulsion in water which is similar to naturally-occurring chylomicrons and is used to simulate turbidity. On the basis of the results from measurements of any one or more of these interferents at a time, in comparison with reference measurements of various levels of interferents, a decision is made concerning whether to reject or accept the sample.

According to another aspect of the present invention, Hb concentration is determined by measurement of reflectance of different wavelengths of light in serum or plasma specimens which are then compared with values obtained through calibration using reference measurements for haemoglobin in serum or plasma samples. Turbidity is determined by measurement of reflectance of different wavelengths of light in serum or plasma specimens which are then compared with values obtained through calibration using serum samples spiked with known amounts of intralipid (IL). Bili and/or BV concentration is determined by measurement of reflectance of different wavelengths of light in serum or plasma specimens which are then compared with values obtained through calibration using reference measurements for Bili and/or BV in serum or plasma samples. On the basis of the results from measurement of any one or more of these interferents at a time, _in comparison with reference measurements of various levels of interferents, a decision is made concerning whether to reject or accept the sample.

In its broad aspect the present invention provides an apparatus for determining specimen integrity of a specimen contained in a primary container where the apparatus comprises: a housing for receiving a sample; a radiation source; a sensor; a means for optically connecting the radiation source with the sensor along a sample path through the housing and along a reference path which by-passes the sample; a means for selectively passing a beam from the sample path and from the reference path to the sensor; and a means for correlating a sensor response, from the sample path relative to a sensor response from the reference path, to a quantity of a known substance in said sample. The housing has a cavity for receiving a sample and a lid for selectively opening and closing the cavity. The radiation source is for emitting a beam of radiation, and the sensor is responsive to receipt of radiation.

In a further aspect the present invention provides an apparatus for determining specimen integrity of a of a specimen contained in a primary container where the apparatus comprises a housing which contains a cavity for receiving a sample and a lid for selectively opening and closing said cavity. It is understood that any means for excluding from the sample, light other than that from the radiation source of the apparatus, is within the scope of this invention. Also, if dark current, i.e., sensor response when sensor is not exposed to the instrument light, is subtracted from both the reference and sample measurements, the room light impinging on the detector can be effectively subtracted without affecting the instrument performance significantly.

The apparatus further comprises a quartz-tungsten-halogen bulb capable of emitting a near infrared, and adjacent visible region light beam having wavelengths from 475 nm to 1080 nm and a beam splitter for splitting the light beam from the quartz-tungsten-halogen bulb into a sample path beam for travel along a sample path and a reference path beam for travel along a reference path. This apparatus further comprises a shutter for selectively blocking the sample path light beam which travels along the sample path and the reference path light beam which travels along the reference path, as well as optical fibre bundles for transmitting the sample path light beam through a sample enclosed in the housing, and optical fibre bundles for transmitting the sample path light beam from the sample to a beam combiner. The beam combiner combines the beam from the sample path and the beam from the reference path into a combined beam. The combined beam of this apparatus is then passed onto a sensor. This apparatus further comprises a series of mirrors along the reference path and the sample path to optically connect the near infrared, and adjacent visible region light source with the sensor, and a grating for dispersing the combined beam into component wavelengths which are passed onto the sensor. The sensor of this apparatus is a photodiode array comprised of a plurality of pixels wherein each of the pixels is set to measure one of a plurality of predetermined light frequencies. Based on the measurement of the frequencies, the sensor generates a plurality of signals wherein each of the signals is responsive to an amount of radiation received by each of the pixels. This apparatus further comprises an analog-to-digital converter to generate digital information from the plurality of signals and a microprocessor, which is connected to the convertor, to correlate the digital information to a quantity of a known substance in the sample.

In a further aspect of the present invention the apparatus provides a means for determining specimen integrity of a of a specimen contained in a primary container by determining the concentrations of a known substance which is selected from a group comprising haemoglobin, bilirubin, _biliverdin and intralipid.

In yet a further embodiment of the present invention a method is provided for determining serum and plasma specimen integrity of a specimen contained in a primary container, wherein the method comprises the following steps. First, transmitting a beam of radiation along a sample path through a sample and along a reference path by-passing the sample. Next, selectively receiving the beam of radiation from the sample path and the reference path, and analyzing the received beams of radiation from the sample path and from the reference path for an amplitude of at least one predetermined light frequency. Finally, correlating the amplitude of the at least one predetermined light frequency with a quantity of a known substance.

In a further aspect of the present invention there is provided a method for determining serum and plasma specimen integrity of a specimen contained in a primary container, wherein the method allows for the determination of the concentrations of a known substance which is selected from a group comprising haemoglobin, bilirubin, biliverdin and intralipid.

In a further embodiment of the present invention there is provided a method whereby the method for determining serum and plasma specimen integrity of the present invention is carried out on one apparatus of the present invention and a second apparatus is used, based on the calibrations of the first apparatus to provide accurate determinations of interferents on the second apparatus, without calibration of the second apparatus.

In yet a further embodiment of the present invention there is provided a method whereby specimen integrity may be determined on a variety of primary specimen container types without recalibration of the apparatus in use to determine interferent concentration and type. Such container types include pipette tips, PVC tubing, as well as tubes, cuvettes, syringe barrels all made of plastic or glass materials.

In a further embodiment there is provided a method for measuring the concentration of interferents in specimens contained in different container types using different analyzers without calibrating the subsequent analyzers for container type or the different analyzer.

In still another aspect of the present invention, a method for rejecting a sample contained in a sample container from further clinical assay based on determining the concentration of at least one interferent in the sample, comprises the steps of:

positioning the sample container in a spectrophotometer such that the sample can be irradiated by the spectrophotometer;
  irradiating the sample with at least one frequency of radiation;
  correlating absorbance of the radiation by the sample with a standard for the interferent(s) to determine the concentration of the interferent(s);
  and
  rejecting the sample if the concentration of the interferent(s) exceeds a predetermined criteria.

Yet another aspect of the present invention provides a method for rejecting a plasma sample contained in a sample container from further clinical assay based on determining the concentration of at least one interferent in the sample, where the method comprises the steps of:

positioning the sample container in a spectrophotometer such that the plasma sample can be irradiated by the spectrophotometer;
  irradiating the plasma sample with at least one frequency of radiation;
  correlating absorbance of the radiation by the plasma sample with a standard for the interferent(s) to determine the concentration of the interferent(s) including calculating the first derivatives of at least two portions of a spectrum generated from a scan for a particular interferent which are used in an algorithm in respect of the interferent(s) to calculate the particular interferent(s) concentration(s); and
  said algorithm(s) in respect of hemoglobin, bilirubin and intralipids are, respectively:
   a. In [(g/L hemoglobin)+1]=7.58(603 nm)+11.75(679 nm) 21.50(1,044 nm)+0.31
     where (Xnm) is the first derivative of the value of an absorbance measured at the wavelength specified;
   b. $\mu$moles/L bilirubin=−3601(641 nm)+3415(662 nm)+ 12710(731 nm)−8214(763 nm)−120
     where (Ynm) is the first derivative of the value of an absorbance measured at the wavelength specified; and c. In (g/L intralipids)=1.53(975 nm)−8.48 where (Znm) is the raw absorbance measured at the wavelength specified; and rejecting the plasma sample if the concentration of the interferent(s) exceeds a predetermined criteria.

Another aspect of the present invention features a method for rejecting a sample contained in a sample container from further clinical assay based on determining the concentration of at least one interferent in the sample, where the method comprises the steps of:

positioning the sample container in a spectrophotometer such that the sample can be irradiated by the spectrophotometer;

irradiating the sample with at least one frequency of radiation;

correlating reflectance of the radiation by the sample with a standard for the interferent(s) to determine the concentration of the interferent(s); and rejecting the sample if the concentration of the interferent(s) exceeds a predetermined criteria.

DESCRIPTION OF THE INVENTION

Figure 1:
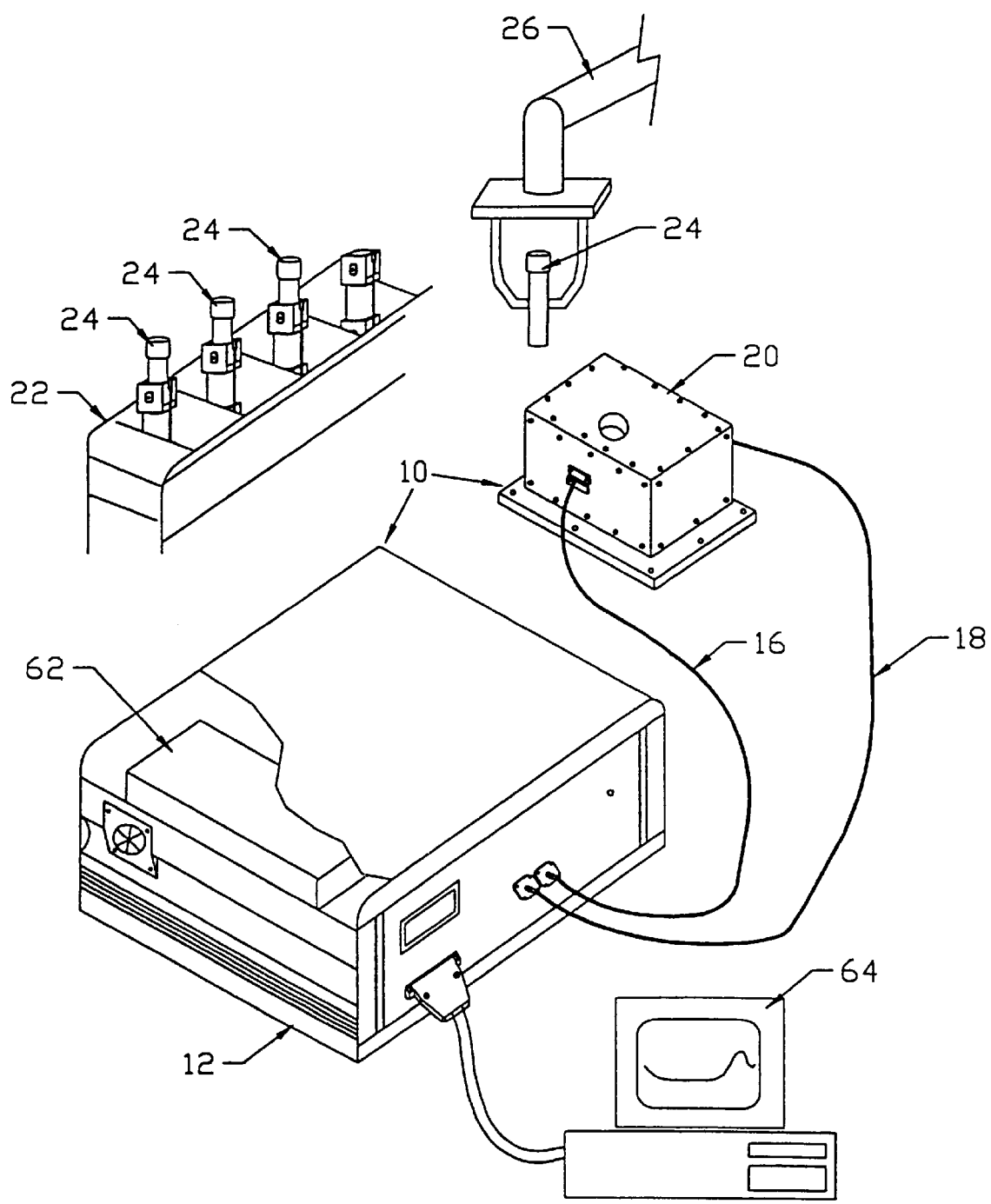
FIG. 1 is a perspective view of a system incorporating an apparatus of the present invention for analyzing specimen integrity.

A system incorporating the apparatus of the present invention is generally illustrated in FIG. 1. The apparatus 10 generally comprises a spectrophotometer 12 optically coupled to, or communicating with a sample head or sample holder 20 through fibre optic bundles 16, 18. Apparatus 10 is mounted or installed adjacent to an automated conveyor 22 which carries a plurality of sample tubes 24. A robotic arm 26 is installed to transport a primary specimen tube 24 between the conveyor 22 and the specimen head 20. It is understood that other conveyor transport mechanisms could be employed and are within the scope of the present invention. Also, the input and output fibre optic bundles 16, 18 can be configured to advance toward the serum or plasma specimen container on the conveyer line thereby eliminating the use of a robotic arm to move the specimen container. Furthermore, any means by which the input and output fibre optic bundles are brought into alignment for measurement of absorption or reflectance in a specimen container is within scope of the present invention.

The fibres optic bundles 16, 18 which traffic radiation to and from the sample, respectively, allow the bulk of the instrumentation to be placed remotely from the specimens.

Figure 2:
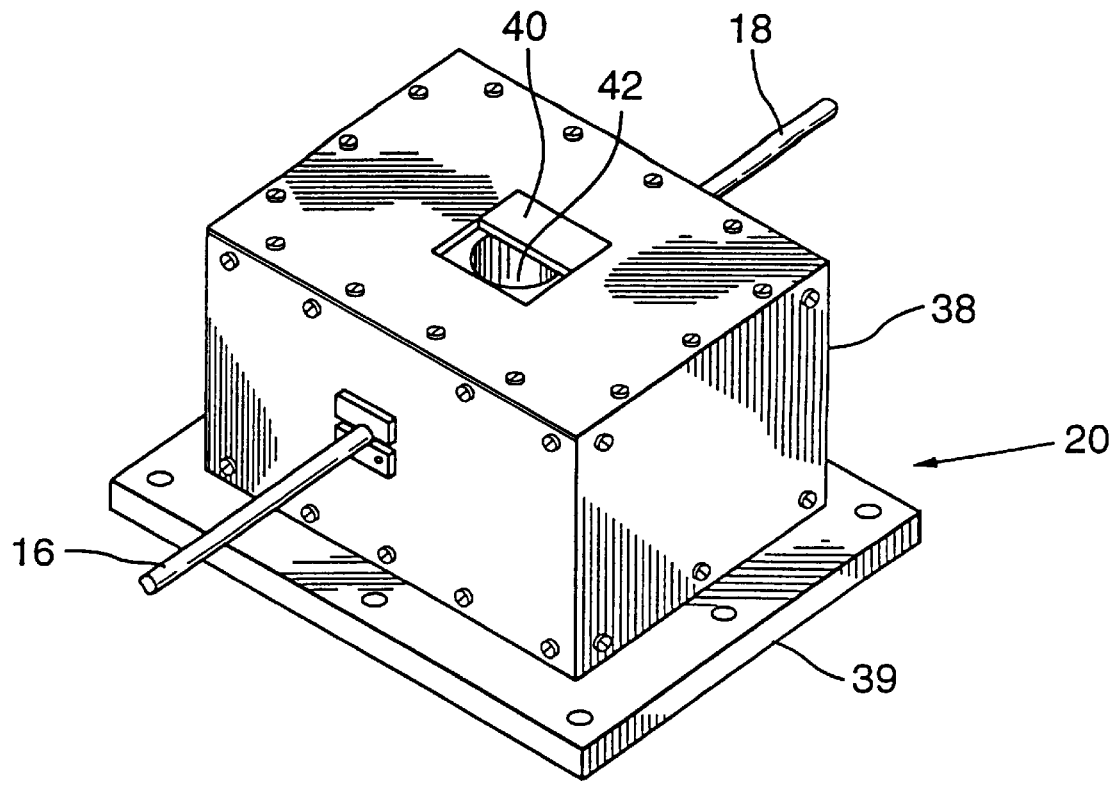
FIG. 2 is a perspective view illustrating the sample head of the apparatus of FIG. 1.
Figure 3:
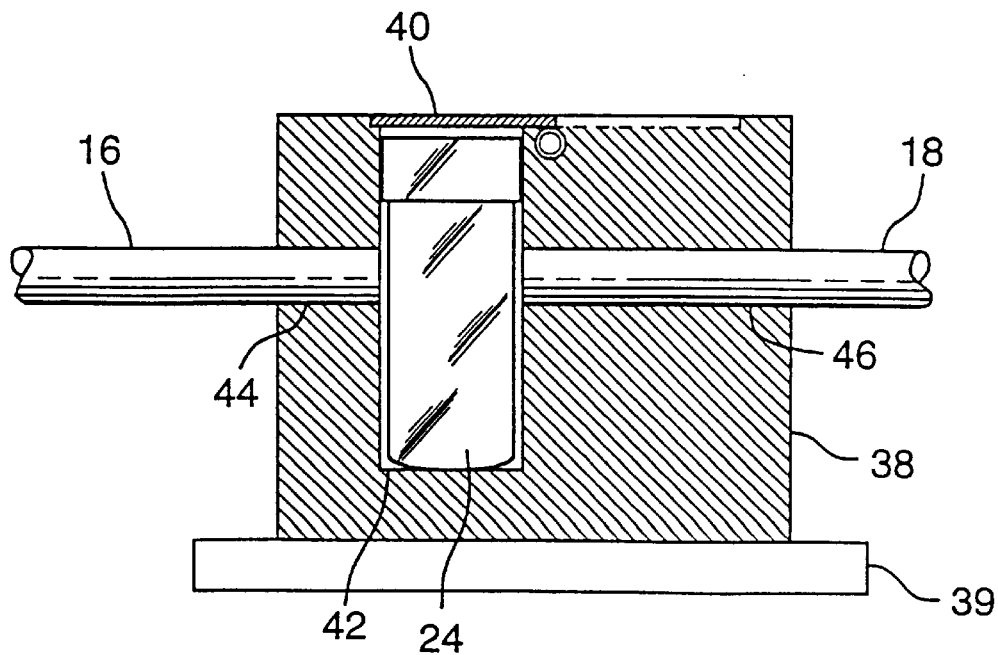
FIG. 3 is a sectional view illustrating the sample head of the apparatus of FIG. 1.

Referring to FIGS. 2 and 3, the sample head 20 is illustrated in greater detail. Sample head 20 comprises a canister 38 having a lid 40 preferably mounted for sliding back and forth to open and close cavity 42. Canister 38 is mounted on a platform 39 for support.

Fibre optic bundle 16 extends through a bore 44 in a wall of canister 38 such that the end of fibre optic bundle 16 communicates with cavity 42 to transmit radiation therein. Similarly, fibre optic bundle 18 extends through a bore 46 in a wall of canister 38 opposite to fibre optic bundle 16. Fibre optic bundle 18 communicates with cavity 42 to receive radiation impinging upon the portion of fibre optic bundle 18 which communicates with cavity 42.

In a preferred embodiment, the radiation is channelled through an optical fibre bundle 16 to the serum or plasma specimen in a labelled primary or secondary tube 24, and the radiation transmitted through the tube, label and specimen, is received by fibre optic bundle 18 which returns the collected radiation to the spectrophotometer 12.

Figure 4:
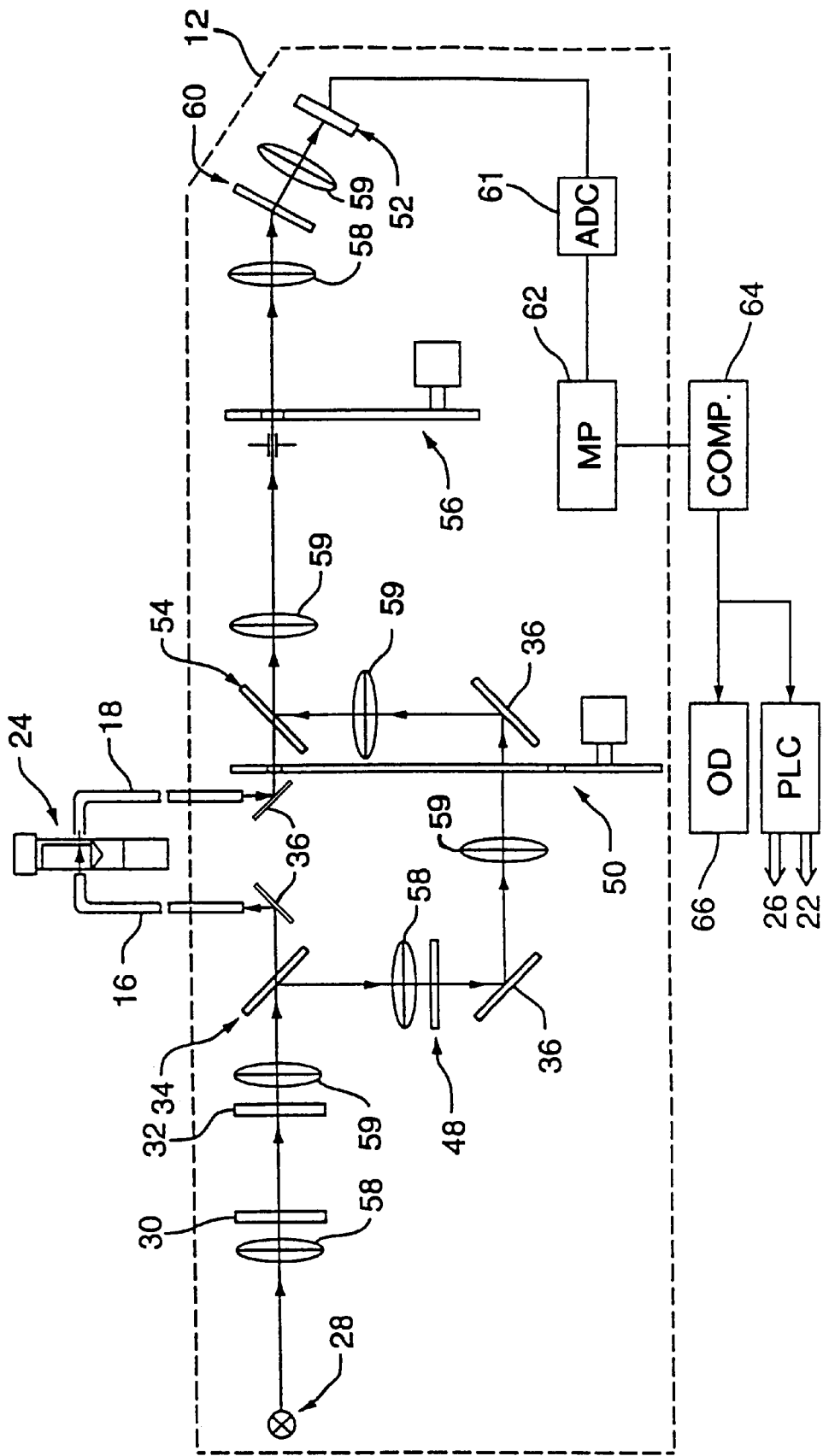
FIG. 4 is a schematic representation of elements of the apparatus of FIG. 1.

Referring to FIG. 4, spectrophotometer 12 has a light source 28. Preferably the light source is a quartz-tungsten-halogen 50 watt lamp. The light source is preferably powered by a stabilized alternating current supply. However, a direct current power supply may also be used depending upon the location or requirements.

The spectral output from light source 28 is broadband covering the visible and NIR regions. The beam of radiation from light source 28 is directed through a first collimating lens 58 then through a band-pass filter 30 to reduce unwanted radiation outside of 450–1080 nm and through a shape-filter 32 to "flatten" the system optical response. This radiation is passed through a first focussing lens 59 and the beam of radiation then proceeds through a beam splitter 34, which in a preferred embodiment is a BK7 glass window.

At the beam splitter 34, a portion of the beam of radiation is directed along a sample path through the fibre optic bundle 16, through the sample contained within tube 24 and back through optic fibre bundle 18. Another portion of radiation is directed along a reference path through a second collimating lens 58 then through a neutral density filter 48, by-passing the sample. Mirrors 36 direct the two portions of the beams of radiation along respective paths. A beam shutter 50 selects which of the beams of radiation are to be passed. These two paths for the beams of radiation are combined at a beam combiner 54, which in a preferred embodiment is a BK7 glass window.

A lamp shutter 56 turns the optical radiation arriving from the beam combiner 54 "on" or "off" to a sensor or a linear photodiode array (PDA) 52. A dispersing element or grating 60 separates out the component wavelengths. In a preferred embodiment dichromated gelatin is used as the grating material.

Various lenses 58 serve to collimate, while various lenses 59 serve to focus the spectral output at several points along the respective paths.

In a preferred embodiment, about 89% of the returning radiation beam is transmitted from the sample path to the spectrophotometer, and about 11% from the reference is reflected and directed into the spectrometer.

Spectrophotometer 12 is preferably a dual beam spectrophotometer with a fixed integration time for the reference beam and a choice of integration time for the sample beam.

The beams of radiation are focused by lenses 58 onto the PDA 52. Each element or pixel of the PDA is set to receive and collect a predetermined wavelength. In a preferred embodiment the PDA 52 comprises 256 pixels. The pixels are rectangular shaped to optimize the amount of optical radiation detected.

When in use, each pixel or wavelength portion is measured approximately simultaneously during a particular scan. The optical radiation falling on each sensor element is integrated for a specified time and the individual pixels, or wavelengths are sampled sequentially by a 16 bit analog-to-digital convertor or ADC.

Although the present embodiment details use of a PDA, any alternative means which achieves this result is within the scope of the present invention. For example a filter-wheel system may be used. In carrying out measurements each analyte uses from one to four wavelengths or pixels. Given that the first derivative of absorbance with respect to measurements with the PDA is the difference between the absorbance at two adjacent pixels, the first derivative of absorbance at one wavelength with a filter-wheel system will require the absorbance measured with two different narrow band-pass filters. It will be readily understood by those skilled in the art that the filters do not need to be assembled on a rotating wheel, but that any structure which achieves the result of a narrow band-pass filtration of absorbed radiation is within the scope of the present invention.

Although the near infra-red region of the electromagnetic spectrum is generally considered to be the interval extending from 650 nm through to 2,700 nm, the nominal wavelength range of a preferred embodiment is from 450 nm to 1,080 nm, which is referred to herein as the "near infrared and adjacent visible region".

Transmission is preferred over reflectance because there is little variation in absorbance due to the tubes in which the serum or plasma specimens reside or due to any labels on the tubes and as such do not significantly affect transmission results. However, it is understood that determination of the concentration of interferents using reflectance is within the scope of this invention. Further, the variation in apparent absorbance due to markings on the labels can be handled effectively by using the first derivative of the absorbance when the amount transmitted is measured.

The PDA integrates the optical radiation over a specified time and converts the optical signal to a time multiplexed analog electronic signal called a scan where absorbance is calculated as:

$$\text{Absorbance} = \log(\text{Reference}_i/\text{Sample measurement}_i) + \log(\text{ITS}/\text{ITR})$$

where

Reference$_i$=reference pixel i readings;

Sample measure$_i$=sample measurement pixel i reading;

ITS=Integration time for sample measurements;

ITR=Integration time for reference measurements; and i=the particular pixel in the PDA.

In respect of these calculations, absorbance can also equal $$\log(\text{Reference}-\text{reference dark measurement}/\text{sample measurement}-\text{sample dark measurement}) + \log(\text{ITS}/\text{ITR})$$

The disadvantage of taking a sample dark and a reference dark measurement is the increase in resting time of the sample on the conveyer. Consequently, depending upon the setting and the criticality of timing, the measurement of a reference dark and sample dark values may or may not be undertaken.

The electronic signal is proportional to the time that the sensor integrates the optical signal. The electronic signal is amplified by analog electronic amplifiers and converted to a digital signal by an analog-to-digital converter or ADC 61. The digital information from the converter 61 is interpreted for data analysis by a microprocessor or MP 62 which is in turn connected via an RS232 connector to a computer 64 or COMP. The results of the data analysis can be shown oil an output device (OD) 66 such as a display and on a printer. A user can control the device to specify a particular interferent to be analyzed and to determine the number and timing of measurements.

Although a rapid pre-screening device could take as much time as one to two minutes per sample measurement and still be considered rapid in this field of art, the present invention allows for rapid pre-screening of samples by taking successive sample measurements at intervals of 5 seconds for all 4 interferents. For example, a robot arm 26 will remove successive samples from a conveyor line 22 for measurement. Samples removed from the conveyor line 22 are inserted into a canister 38 with a lid 40 which is closed to shield the sample from extraneous light. The sample is then measured; the sample holder 20 opened; the sample is placed according to the controlling process which may include acceptance or rejection of the, sample for further analysis; and another sample is picked up by the robotic arm and placed into the sample holder to allow for another measurement. This set of operations takes 5 seconds. The controlling process includes flagging any assays run on a clinical analyser using samples from the containers measured according to the method of the present invention if the results of the measurements in the primary containers exceed predetermined thresholds for any of the interferents measured.

The integration time for the sample beam is low for clear sample since there is less scattered light and therefore more light is transmitted to the detector 52. When the light is sufficiently scattered by, for example a turbid sample, the spectrophotometer 12 will automatically switch to a higher integration time. The higher integration time chosen will be within a pre-selected range, such that the detector's response is optimal. This feature will allow all samples, from the clearest to the most turbid, to be efficiently screened without exceeding the linear response range of the detector. In other words, the integration time for said sample beam is low for clear samples and is automatically switched to a higher integration time for turbid samples.

In a preferred embodiment, measurements can be taken where the sample is contained in a sample tube which carries a sample identification, or similar type of label. In addition, it is understood that this invention can be used with all varieties of sample tubes used in the blood collection and analysis field. Furthermore, it is understood, as illustrated in this specification, that the spectrophotometer in use can be calibrated using one sample tube type and measurements for determining the concentrations of interferents of a sample in a different container type, such as a pipette tip, may be carried out without recalibration of the spectrophotometer.

As with any quantitative method, calibration of the spectrophotometer is required. However the method for NIR calibration is much more complex than most which can be calibrated with a minimum of a single standard material of known concentration. In respect of NIR calibration, samples must contain all interferents expected during the analysis of an unknown sample; the sample must contain an even distribution of the interferent of interest, and the concentrations of any two interferents should not correlate significantly. It is to be understood, that for any pre-screening, according to the present invention, of a typical sample for subsequent analysis, all interferents may be present. The pre-screen allows for the determination of the concentration of any one in the presence or absence of the others.

The first part of the process for generating a calibration curve is to store spectral data for the calibration set. The calibration algorithm for each interferent must be installed in a microprocessor so that when an unknown sample is tested for a particular interferent the result is quickly produced. In order to calculate the quantity of any interferent present, any one of several different methods, all of which are within the scope of this invention, may be used.

One approach would be to use multiple linear regression and choose wavelengths using standard procedures and statistics to find optimal wavelengths at which to describe concentrations of interferents. However significant changes in the spectrum brought about by lipemia, influence the outcome of calculations for haemoglobin or for bilirubin, or biliverdin, and consequently it is necessary to select additional wavelengths to compensate for these interactions. Nevertheless, this is not a preferred approach.

Another method which may be employed is to use all of the spectrum, and perform either a principal component analysis or partial least squares analysis and effectively determine from the components that are optimised the concentration of these different elements. However, a disadvantage of using either of these methods is that they are computationally intensive and consequently take more time to calculate and increase the length of time required to assess each sample.

A preferred method is to calculate the first derivative of certain portions of the spectra in respect of the particular interferent being measured. It is also possible to calculate the second, or third derivatives, and such calculations are within the scope of this invention. However, each step of taking differences to calculate those derivatives is more time consuming and introduces more noise.

In practice, an optimal combination of first derivatives of at least two portions of a spectrum generated from a scan for a particular interferent are used to calculate interferent concentration. The precise approach used depends on the interferent being measured. Thus, from the above, it is clear that the correlating includes calculating the first derivatives of at least two portions of a spectrum generated from a scan for a particular interferent which are used in an algorithm in respect of the interferent(s) to calculate the particular interferent(s) concentration(s); wherein the first derivative of absorbance is used to correlate said quantity of interferent.

In respect of Hb optimal results may be obtained by calculating the first derivative of measurements at wavelengths of approximately 603 nm, 679 nm and 1044 nm. To minimize errors in measurements X in the regression analysis, is replaced with $\ln(1+X)$ where X is g/L of Hb. In lipemic or turbid samples measurements are taken at wavelengths in the region of about 975 nm which is a water peak. 975 nm is chosen because significant absorbances due to Hb, Bili and BV do not occur in this region. The transformation of X to $\ln(1+X)$ is not necessary for all sample containers as demonstrated below by the second calibration algorithm for Hb.

Since turbidity or lipemia is mainly due to chylomicron particles, turbidity may be simulated by adding IL tb clear serum or plasma; IL is an emulsion of fat particles similar to naturally-occurring chylomicrons. In respect of IL, results may be obtained by using the raw absorbance measurements at a wavelength of approximately 975 nm. Although the subsequent discussion deals with the raw absorbance measurement it is understood that the first derivative of the measurement at this wavelength may be used and is within the scope of the present invention. This is illustrated in the present disclosure where the first derivative of the measurement is used in respect of the IL data presented in Table 1 and Table 2. Indeed, the first derivative of absorbance is preferred because any markings on a label or a dirty label will result in over estimation of turbidity if the raw absorbance is used for the calculation. Markings or a dirty label on a container wall will diminish the light transmitted to the detector, and will result in an increase in the calculated absorbance. To extend the linear range of calibration, X is replaced by In X where X is g/L of IL. This InX transformation of X is necessary when raw absorbance is used, but is not necessary when the first derivative of raw absorbance is used.

The calibration equations outlined below cover the broad range of variability anticipated for the interferents. If low-end accuracy becomes a concern, separate calibrations can be developed: one for the high end, and a second, if the result predicted by the previous calibration is less than a predetermined level.

In order to calibrate the spectrophotometer for haemoglobin, 58 serum specimens with total bilirubin concentration in the approximate range of 0 to 500 $\mu$mol/L, as estimated by a Kodak Ektachem™, were stored, refrigerated or frozen until used. These samples had no visible homolysis or turbidity. The specimens were run over several weeks on three separate days. IL was added to specimens in the approximate range of 0–5 g/L final concentration, and Hb in the approximate range of 0–6 g/L final concentration. The Hb and IL were added to the 58 specimens to produce an additional 57 samples with various combinations of Bili, Hb and IL. A different patient specimen was used for each Hb addition. The Hb was prepared by removing the plasma and lysing the erythrocytes with an equal volume of lysing reagent. The Hb content of the lysates was measured on a Coulter-STKS™. Five atypical Hbs were included in the sample set. Immediately after the samples were prepared, they were run on a spectrophotometer in different labelled tubes, and the spectra stored on diskettes. The analysis on a sample set of 115 was performed by a statistical computer program and an algorithm developed for Hb.

Figure 5:
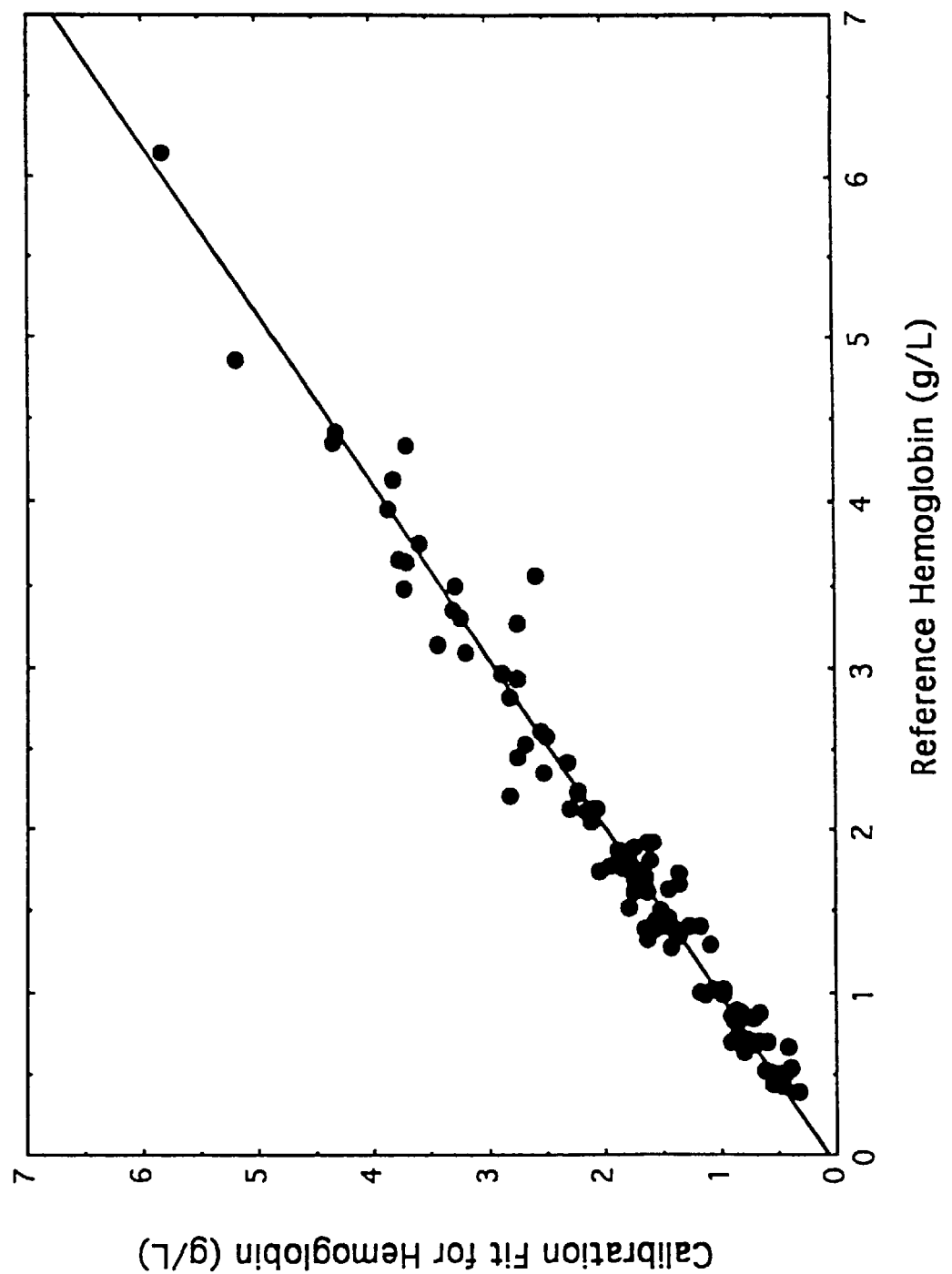
FIG. 5 is a graphic representation of a linear regression fit of data for haemoglobin calibration in units of grams per liter on the abscissa and ordinant axes.

FIG. 5 is a graphic representation of the results of a linear regression fit of the data generated from the Hb calibration. The algorithm which was developed for Hb based on this data is as follows:

$$\ln[(g/L\ Hb)+1]=7.58(603\ nm)+11.75(679\ nm)-21.50(1{,}044\ nm)+0.31$$

where (Xnm) is the first derivative of the absorbance measurement at the wavelength specified.

Figure 6:
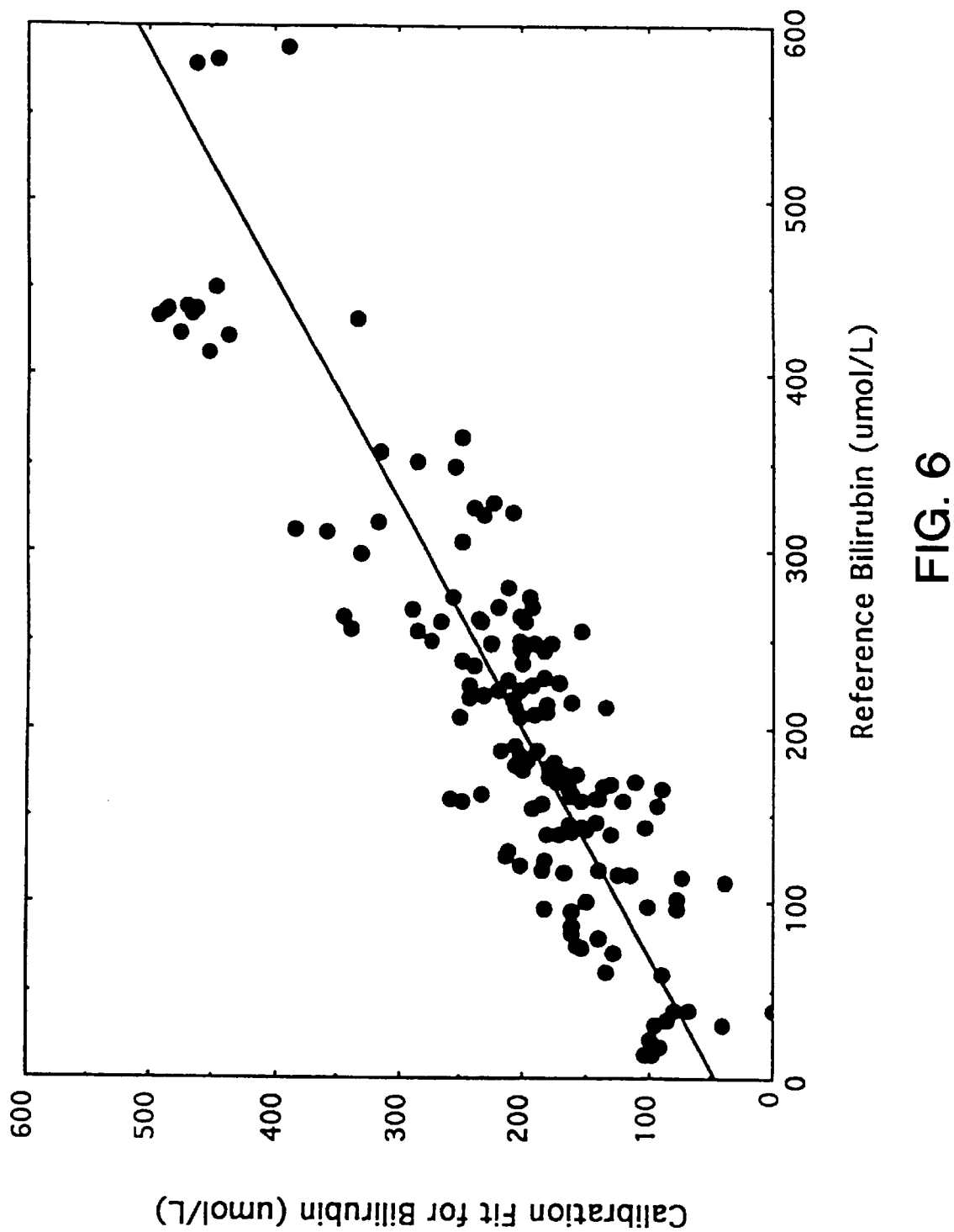
FIG. 6 is a graphic representation of a linear regression fit of data for total bilirubin calculation in units of micromoles per liter on the abscissa and ordinant axes.

With respect to generating a calibration curve for bilirubin, the spectra for the initial 58 specimens which were already stored, as discussed above, were included in this sample set. From these specimens, an additional 94 samples were obtained by adding varying amounts of Hb and IL. These spectra were also stored, and the initial Bili concentrations were adjusted for the dilutional effects of the Hb and IL. The data generated from this calibration were fitted by linear regression analysis and presented as a graphic representation in FIG. 6.

A similar analysis on this sample set of 152 was performed as before and the algorithm developed for Bili on the basis of this data is as follows:

$$\mu moles/L\ Bili=-3601(641\ nm)+3415(662\ nm)+12710(731\ nm)-8214(763\ nm)-120$$

An alternative algorithm for Bili is:

$$mg/dL\ Bili=142.09(511\ nm)+89.9(554\ nm)-4.47$$

where (Ynm) is the first derivative of the absorbance measurement at the wavelength specified.

Figure 7:
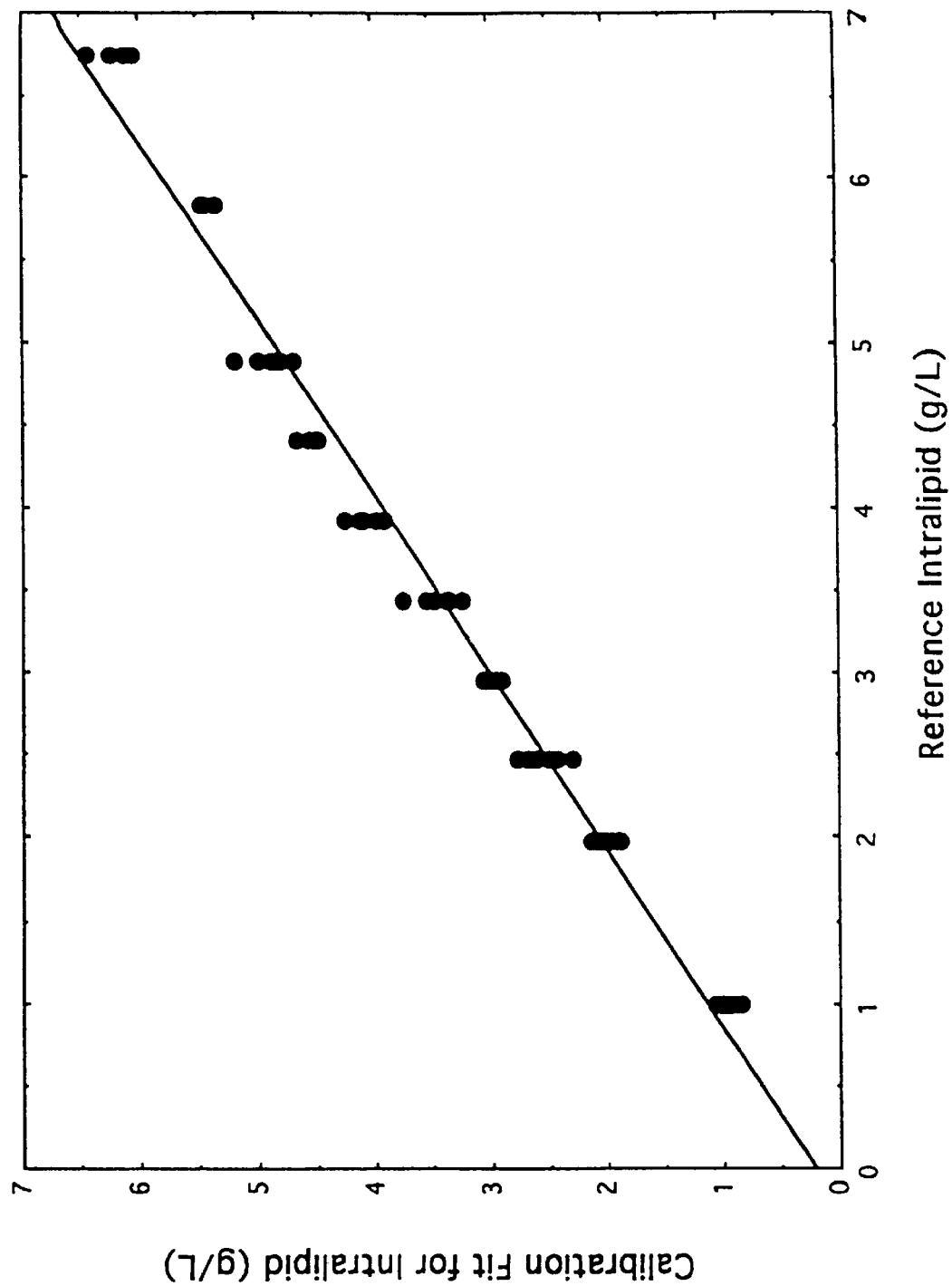
FIG. 7 is a graphic representation of a linear regression fit of data for turbidity calibration in terms of intralipid concentration in units of grams per liter on the abscissa and ordinant axes.

In respect of calibration for turbidity, 39 of the initial 58 samples were spiked with varying amounts of IL, and their absorbance spectra stored in a manner similar to as described above. The data generated from this calibration were fitted by linear regression analysis and presented as a graphic representation in FIG. 7. As well, a similar analysis on this sample set of 39 was performed as described above, and an algorithm was developed for turbidity in terms of equivalent IL concentration. This algorithm is as follows:

$$\ln(g/LIL)=1.53(975\ nm)-8.48$$

where (Znm) is the raw absorbance measurement at the wavelength specified.

An alternative algorithm for IL is:

$$g/L\ IL=256.29(874\ nm)+0.17$$

where (Znm) is the first derivative of absorbance measurement at the wavelength specified.

Thus, the method described above is one wherein the frequencies of radiation are 603 nm, 679 nm and 1044 nm all of which are used to correlate to quantities of hemoglobin; 641 nm, 662 nm, 731 nm, and 763 nm all of which are used to correlate to quantities of bilirubin; and 975 nm which is used to correlate to quantities of intralipids.

As will be readily understood by those skilled in the art, several algorithms can be developed for each interferent using different groups of wavelengths with the resultant prediction performance by the different algorithms for the same interferent being similar.

In addition we have also developed a method that allows for the use of the algorithms of the present invention, as developed in one spectrophotometer, to be used in a second spectrophotometer without requiring calibration of the second spectrophotometer. As is readily appreciated by those skilled in the art, calibration of a spectrophotometer is a time consuming process. The method presented here avoids this requirement and consists of using the algorithms from the first spectrophotometer on the second spectrophotometer, and applying a correction adjustment to the predicted data obtained with the second spectrophotometer. The correction adjustment consists of calculating the slope and intercept from a small set of samples with known concentrations wherein the actual or known concentrations of interferents are plotted on the X axis and the predicted concentrations are plotted on the Y axis. The "predicted concentrations" are obtained by measurement of the known concentrations with the second spectrophotometer and calculation of the predicted concentrations using the respective algorithms from the first spectrophotometer. The expression "small sample set slope" refers to the slope obtained from this same plot. The predicted values as obtained by the second spectrophotometer in respect of samples with unknown concentrations of interferents are then submitted to the following adjustments: the intercept value obtained from a plot of actual versus predicted concentrations, referred to above, is subtracted from the predicted measurement and the result of this subtraction is then divided by the slope obtained of the plot of the actual versus predicted referred to above. This correction adjustment can be represented by the following formula where "small sample set intercept" refers to the intercept obtained from the plot of the actual or known concentrations of interferents on the X axis versus the predicted concentrations as obtained on the second spectrophotometer on the Y axis:

$$\text{Corrected predicted } Y = \frac{(\text{predicted } Y - (\text{small sample set intercept}))}{(\text{small sample set slope})}$$

Figure 8:
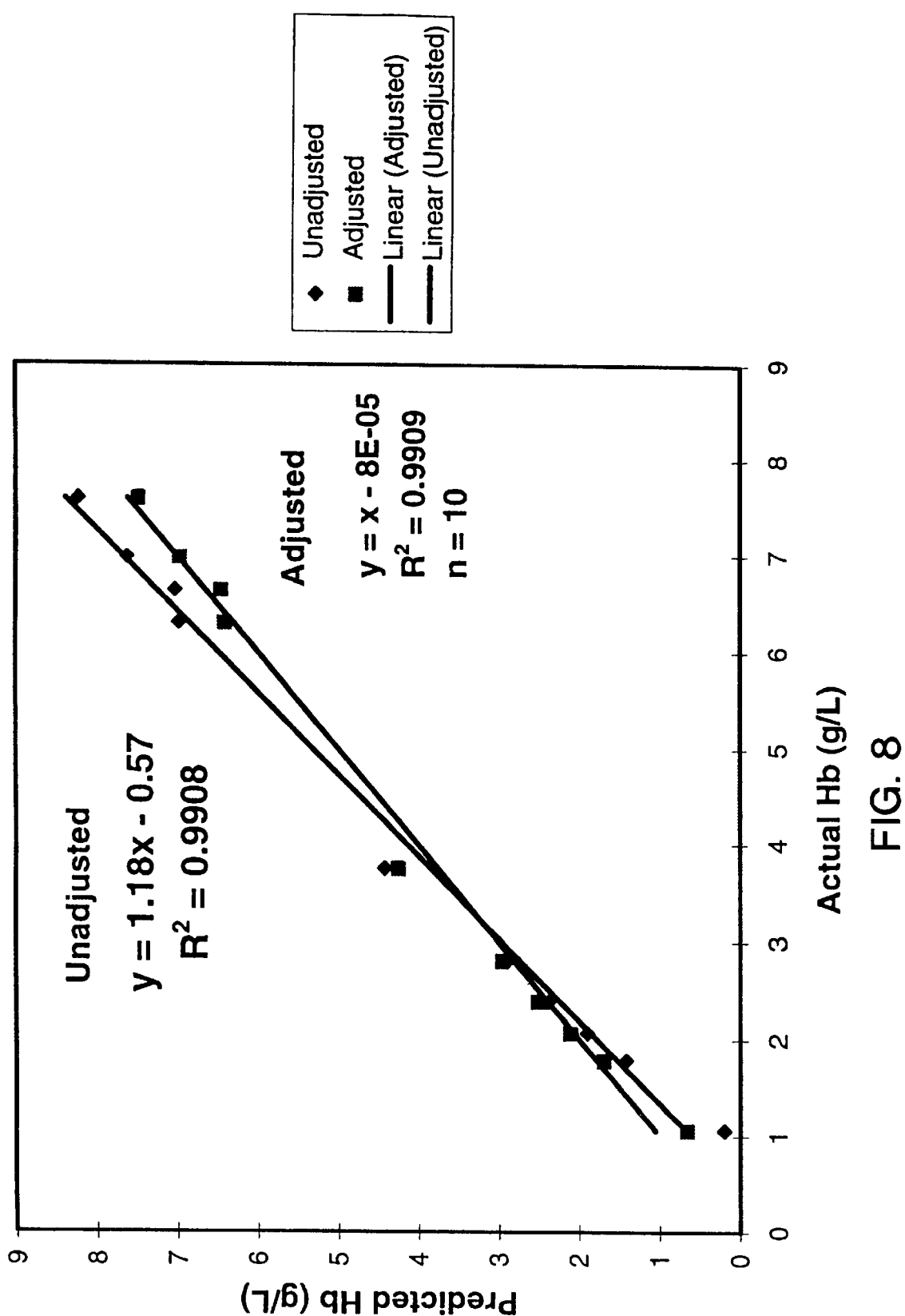
FIG. 8 is a graphic representation of a linear regression fit of data in respect of predicted unadjusted and predicted adjusted haemoglobin concentration for sample measured on a different instrument.
Figure 9:
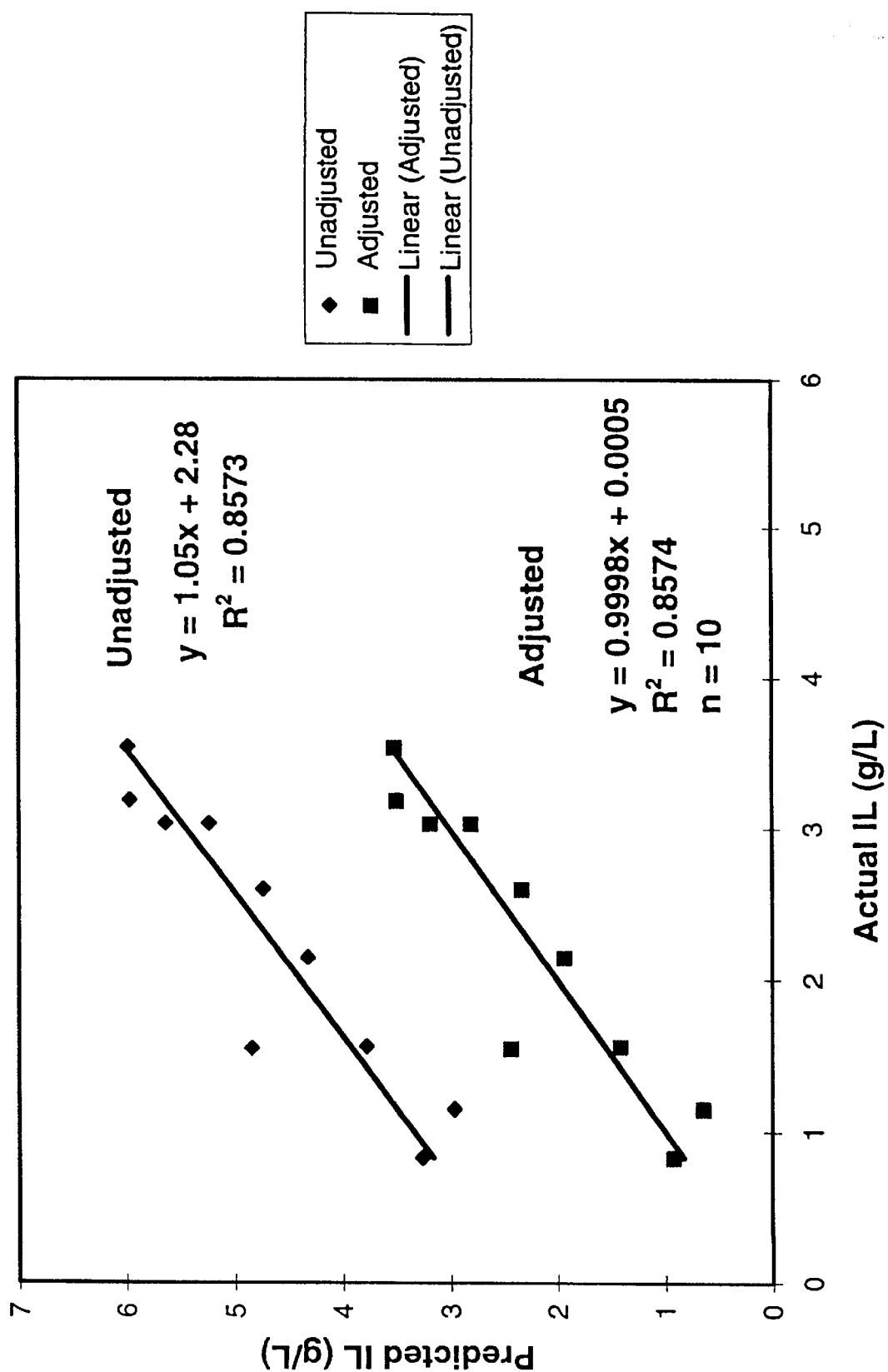
FIG. 9 is a graphic representation of a linear regression fit of data in respect of predicted unadjusted and predicted adjusted intralipid concentration for sample measured on a different instrument.
Figure 10:
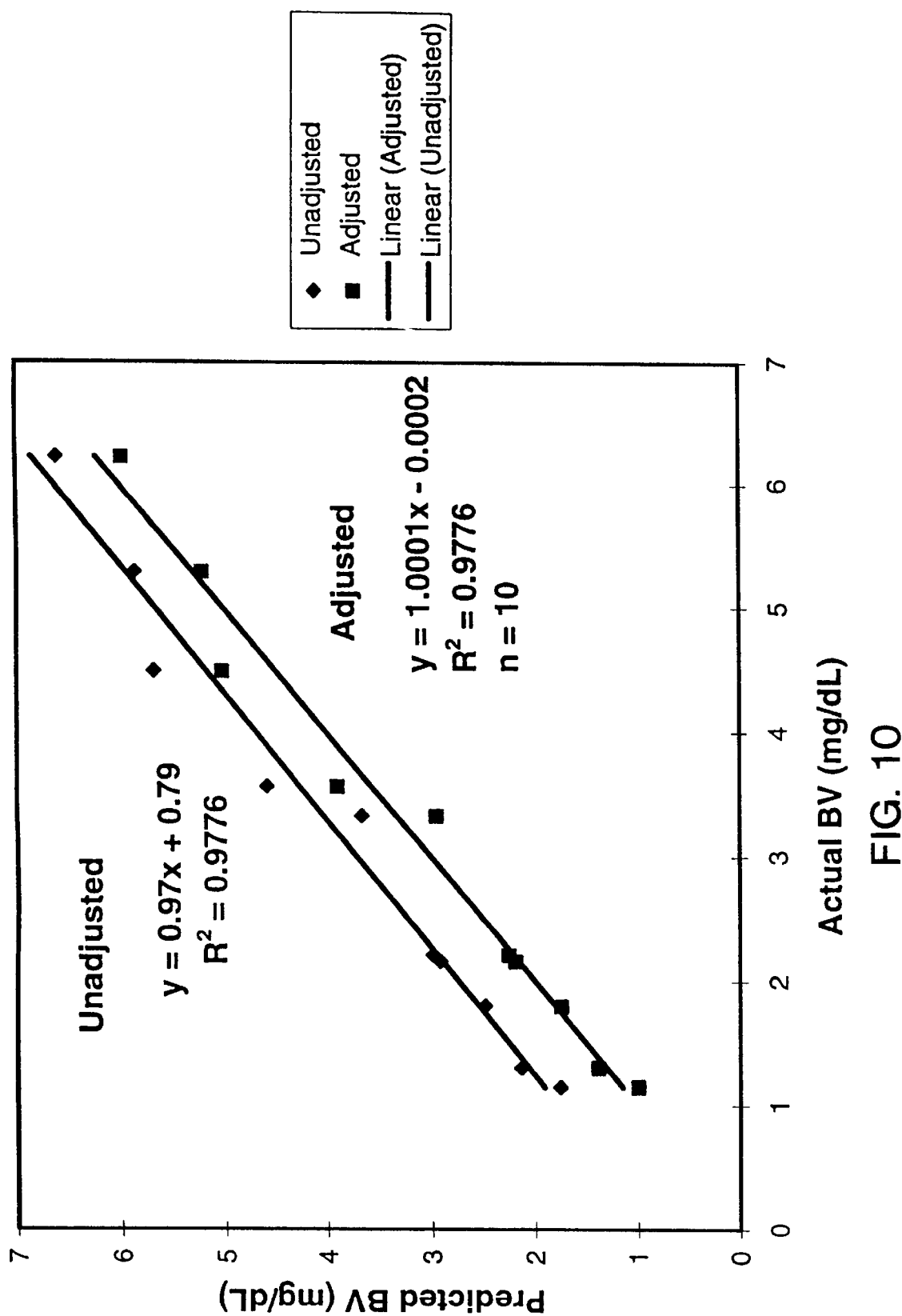
FIG. 10 is a graphic representation of a linear regression fit of data in respect of predicted unadjusted and predicted adjusted biliverdin concentration for sample measured on a different instrument.

An application of the method provided the results presented in Table 1. The Table contains data from samples with known concentrations of haemoglobin, intralipid, and biliverdin and provides "predicted" and "corrected predicted" results from samples measured in a spectrophotometer other than the first spectrophotometer using the calibration set obtained using the first spectrophotometer. The calibration algorithms were developed using the first (a different) spectrophotometer. FIGS. 8, 9, and 10 illustrate the regression analysis with respect to the data obtained and provided in Table 1.

A similar correction to the predicted concentration of interferents can be made when an instrument is calibrated using sample containers of a first type, for example, hard translucent plastic such as a pipette tip made of polypropylene and predicting on the same instrument using sample containers of a second type, for example, soft translucent plastics such as PVC tubing with markings on the surface. Indeed, it is understood and within the scope of this invention that calibration of a spectrophotometer for samples in one container type can be used, without recalibration of the spectrophotometer, on samples in a different container type by making similar adjustments to the predicted results. Furthermore, it is understood that it is within the scope of this invention that calibration of a spectrophotometer for samples in one container type can be transferred to a second spectrophotometer and, on samples in a different container type by making similar adjustments to the predicted results as set out above.

Illustrative of the ability to calibrate using one container type and being able to use that calibration with a different container type is the data set out in Table 2. Table 2 provides data from samples measured in Ektachem™ pipette tips made from polypropylene with known concentrations of haemoglobin, intralipid, and biliverdin.

The calibration equations developed using polypropylene pipette tips are as follows:
Haemoglobin g/LHb=24.14(591 nm)−23.64(617)−0.93

Biliverdin mg/dL BV=120.51(695 nm)+124.77(777 nm)+0.19

Intralipid g/L IL=44.91(992 nm)+222.24(1044 nm)−0.98

Where (Xnm) is the first derivative of the absorbance measurement at the wavelengths specified for all three interferents.

Figure 11:
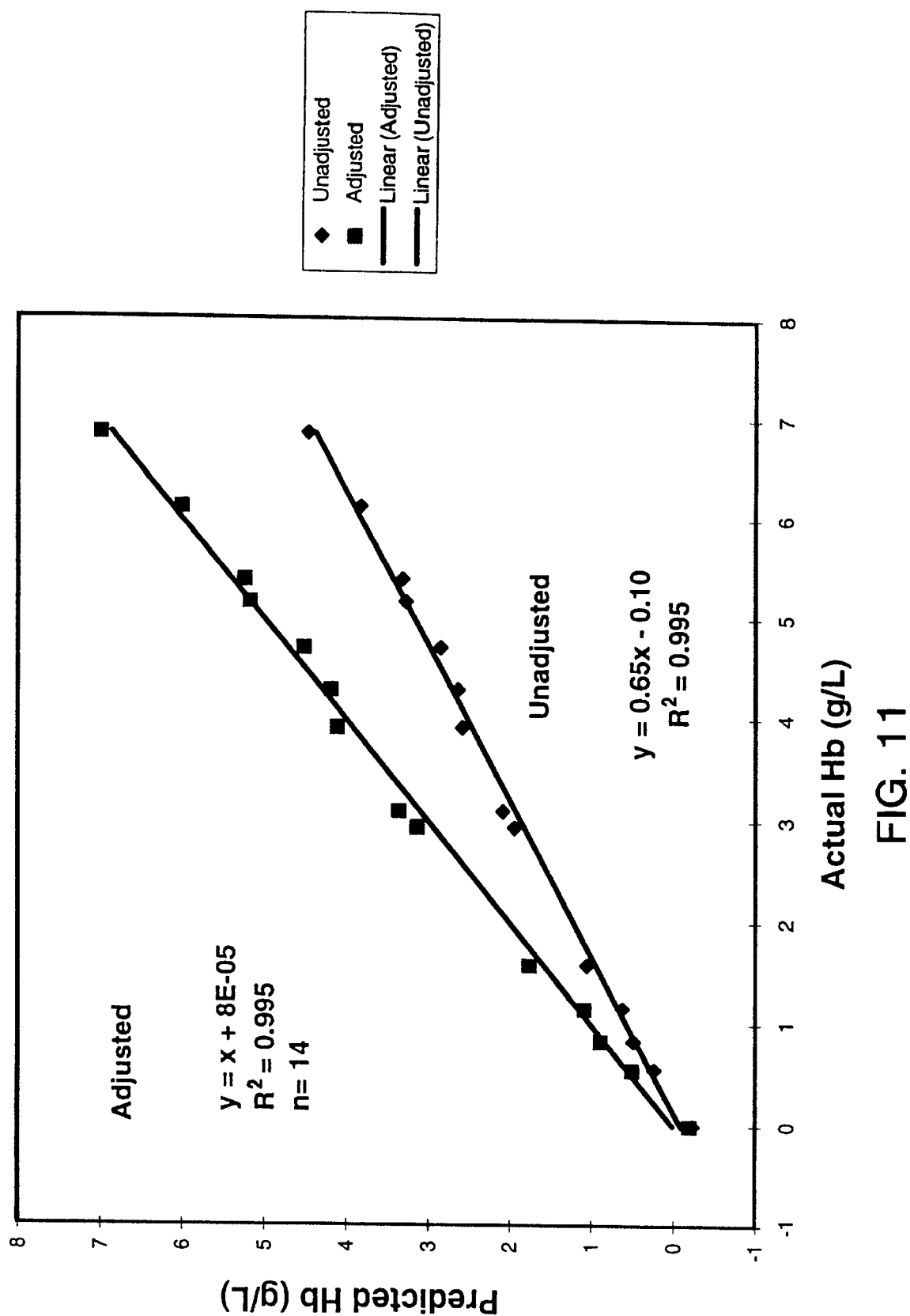
FIG. 11 is a graphic representation of a linear regression fit of data for predicted unadjusted and predicted adjusted haemoglobin concentration for sample in a different container type.
Figure 12:
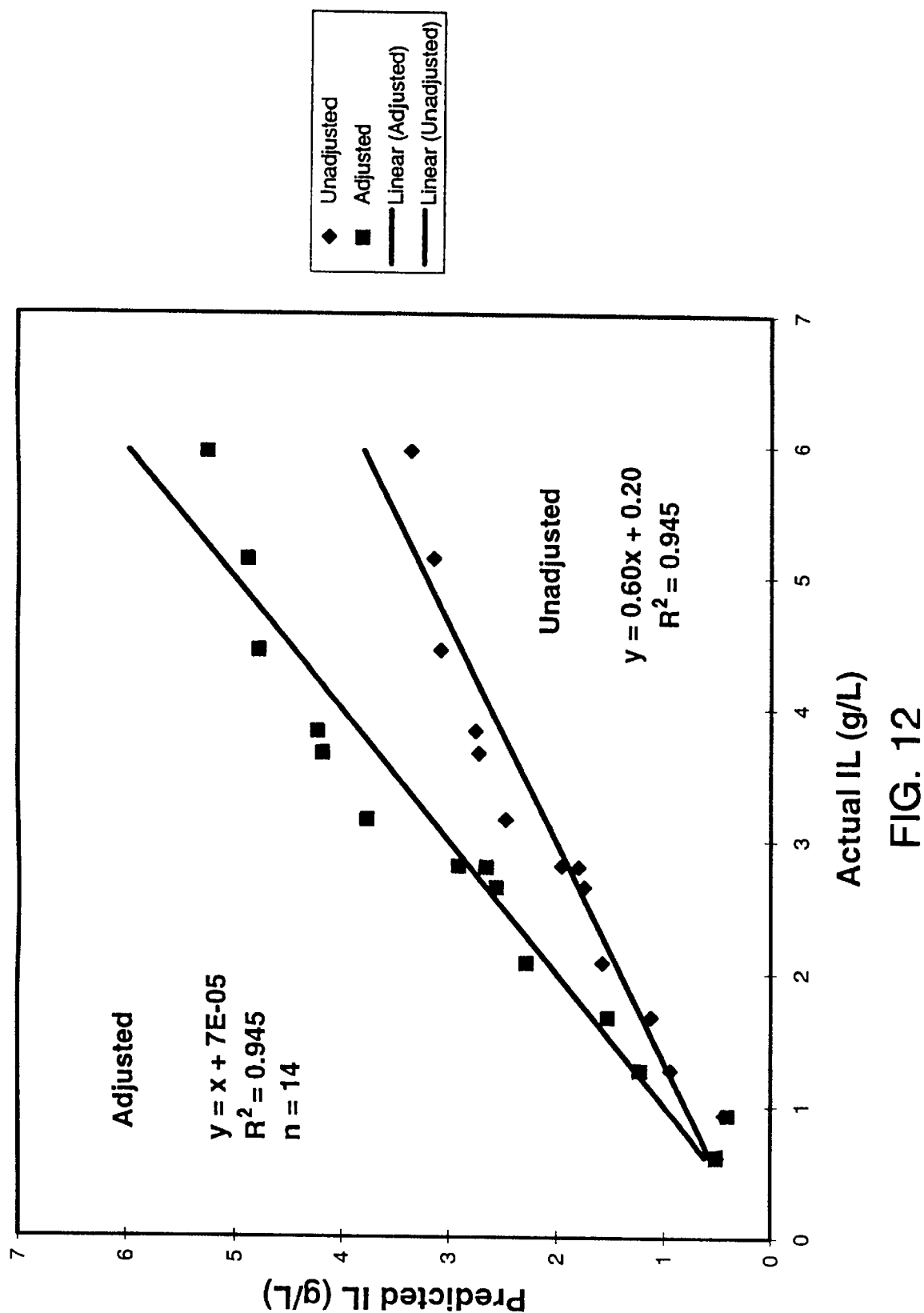
FIG. 12 is a graphic representation of a linear regression fit of data for predicted unadjusted and predicted adjusted intralipid concentration for sample in a different container type.
Figure 13:
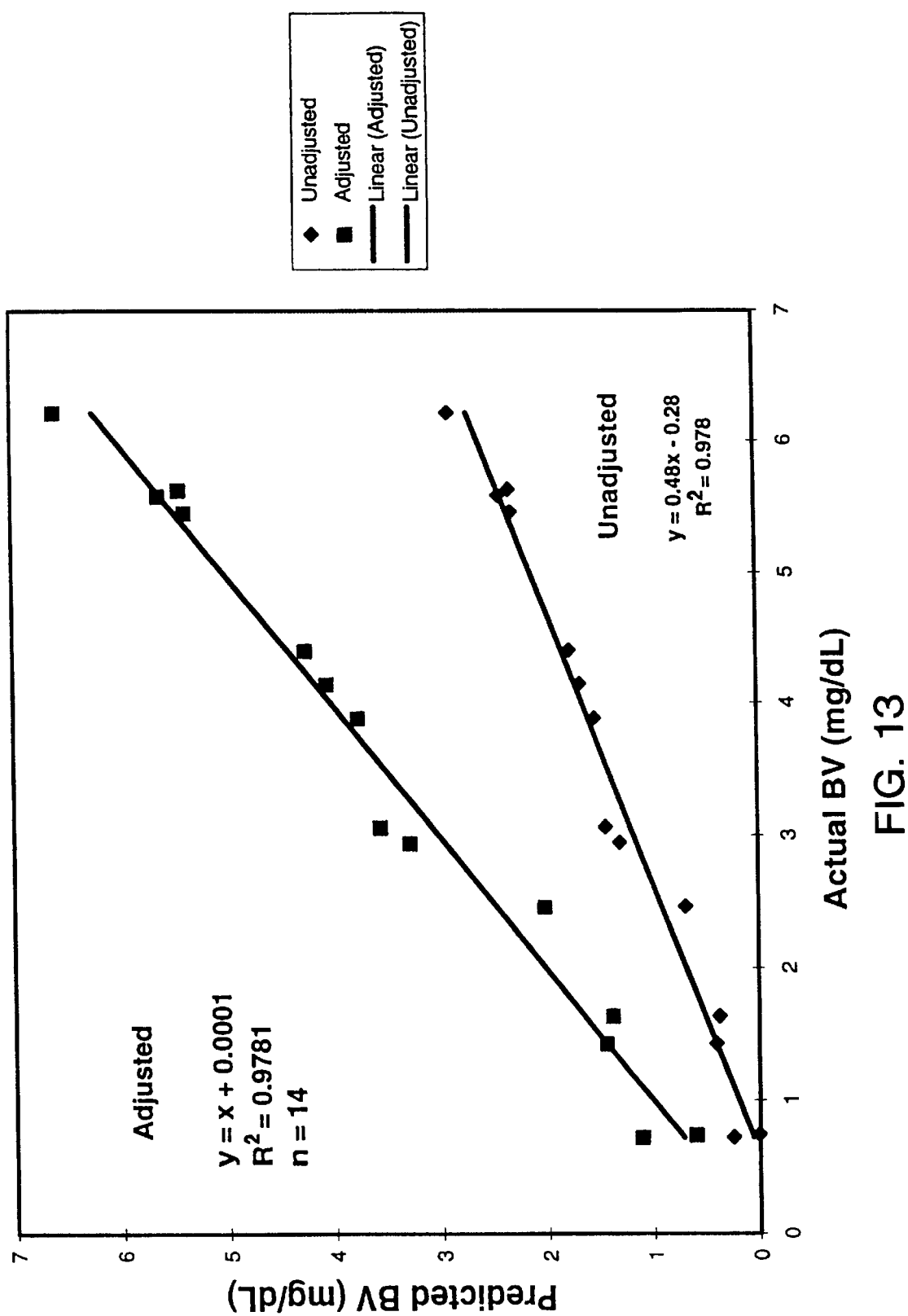
FIG. 13 is a graphic representation of a linear regression fit of data for predicted unadjusted and predicted adjusted biliverdin concentration for sample in a different container type.

Table 2 also provides results using the above calibration set from the pipette tips on the same spectrophotometer for samples contained in PVC tubing with markings on the surface. As with the predicted values in the second spectrophotometer, discussed above, the algorithms developed with the pipette tips are used on the raw data derived from measurements of samples in the PVC tubing to provide a small sample set from which the slope and intercept are obtained. The correction adjustment then consists of calculating the slope ("small sample set slope") and intercept ("small sample set intercept") from a small sample set of known concentrations wherein the actual or known concentrations of interferents are plotted on the X axis and the predicted concentrations of these known concentrations are plotted on the Y axis. These "predicted values" use the calibration curve and algorithms obtained from the first measurements in pipette tips on the same spectrophotometer. With these small sample set intercept and small sample set slope values the predicted set of concentrations obtained from samples with unknown concentrations are corrected by subtracting the small sample set intercept from the predicted value, the result of which is then divided by the small sample set slope to provided a "corrected predicted" concentration. This correction allows for the prediction of concentrations of haemoglobin, intralipid, biliverdin or any other interferents measured according to this invention in one sample container type with a determination of samples in different materials, such as PVC tubing. Illustrated in FIGS. 11, 12 and 13 are the regression fit analyses of the data shown in Table 2 in respect of haemoglobin, intralipid and biliverdin respectively.

With the calibrations and algorithms which can be developed according to the present invention, it is possible to detect and quantify Hb, Bili, Biliverdin, and any other bile pigments as well as IL (as a measure of turbidity), for the purposes of rapidly pre-screening plasma and/or serum samples which will be further analyzed, or in any setting currently employing a visual determination of such parameters. It may also be employed on a retrospective basis where there is a disagreement between test results and the clinical status of a patient.

While the invention has been particularly shown and described with reference to preferred embodiments, it will be understood by those skilled in the art that various other changes in form and detail may be made without departing from the spirit and scope of the invention.

TABLE 1

| | Hemoglobin (g/L) | | | Intralipid (g/L) | | | Biliverdin (mg/dL) | | |
|---|---|---|---|---|---|---|---|---|---|
| Sample # | Known | Unadjusted | Adjusted | Known | Unadjusted | Adjusted | Known | Unadjusted | Adjusted |
| 1 | 6.64 | 7.01 | 6.44 | 2.15 | 4.32 | 1.93 | 3.57 | 4.58 | 3.89 |
| 2 | 1.06 | 0.20 | 0.66 | 3.19 | 5.96 | 3.49 | 5.30 | 5.86 | 5.20 |
| 3 | 1.79 | 1.42 | 1.69 | 1.56 | 3.78 | 1.42 | 3.33 | 3.66 | 2.94 |

TABLE 1-continued

| | Hemoglobin (g/L) | | | Intralipid (g/L) | | | Biliverdin (mg/dL) | | |
|---|---|---|---|---|---|---|---|---|---|
| Sample # | Known | Unadjusted | Adjusted | Known | Unadjusted | Adjusted | Known | Unadjusted | Adjusted |
| 4 | 2.07 | 1.90 | 2.10 | 1.15 | 2.96 | 0.64 | 1.15 | 1.75 | 0.99 |
| 5 | 7.60 | 8.22 | 7.46 | 3.04 | 5.63 | 3.18 | 2.21 | 2.98 | 2.25 |
| 6 | 2.39 | 2.38 | 2.50 | 3.04 | 5.23 | 2.80 | 1.80 | 2.48 | 1.74 |
| 7 | 6.30 | 6.96 | 6.40 | 3.54 | 5.98 | 3.51 | 1.31 | 2.13 | 1.38 |
| 8 | 2.81 | 2.89 | 2.94 | 2.60 | 4.73 | 2.33 | 2.16 | 2.91 | 2.18 |
| 9 | 6.98 | 7.61 | 6.95 | 1.55 | 4.84 | 2.43 | 4.50 | 5.67 | 5.01 |
| 10 | 3.75 | 4.42 | 4.24 | 0.83 | 3.26 | 0.93 | 6.23 | 6.61 | 5.98 |

TABLE 2

| | Hemoglobin (g/L) | | | Intralipid (g/L) | | | Biliverdin (mg/dL) | | |
|---|---|---|---|---|---|---|---|---|---|
| Sample # | Known | Unadjusted | Adjusted | Known | Unadjusted | Adjusted | Known | Unadjusted | Adjusted |
| 1 | 0 | −0.23 | −0.21 | 5.96 | 3.35 | 5.23 | 2.47 | 0.69 | 2.02 |
| 2 | 0.55 | 0.22 | 0.49 | 2.65 | 1.73 | 2.55 | 4.41 | 1.76 | 4.25 |
| 3 | 0.83 | 0.47 | 0.87 | 4.44 | 3.07 | 4.76 | 0.74 | 0.01 | 0.60 |
| 4 | 1.15 | 0.60 | 1.07 | 0.93 | 0.44 | 0.40 | 3.07 | 1.43 | 3.55 |
| 5 | 1.58 | 1.04 | 1.75 | 3.83 | 2.74 | 4.22 | 3.89 | 1.52 | 3.75 |
| 6 | 2.94 | 1.94 | 3.13 | 3.66 | 2.71 | 4.17 | 1.43 | 0.40 | 1.43 |
| 7 | 3.1 | 2.09 | 3.35 | 2.08 | 1.57 | 2.27 | 6.23 | 2.89 | 6.59 |
| 8 | 3.92 | 2.58 | 4.10 | 1.27 | 0.94 | 1.22 | 5.60 | 2.42 | 5.62 |
| 9 | 4.29 | 2.63 | 4.18 | 2.81 | 1.95 | 2.90 | 0.72 | 0.25 | 1.11 |
| 10 | 4.71 | 2.84 | 4.51 | 2.80 | 1.79 | 2.64 | 5.64 | 2.33 | 5.42 |
| 11 | 5.17 | 3.27 | 5.17 | 1.67 | 1.12 | 1.52 | 4.15 | 1.66 | 4.05 |
| 12 | 5.39 | 3.31 | 5.23 | 5.14 | 3.13 | 4.87 | 1.64 | 0.37 | 1.36 |
| 13 | 6.12 | 3.82 | 6.00 | 0.62 | 0.51 | 0.51 | 5.47 | 2.30 | 5.38 |
| 14 | 6.86 | 4.46 | 6.99 | 3.16 | 2.46 | 3.76 | 2.95 | 1.29 | 3.28 |

We claim:

1. A method for rejecting a sample contained in a sample container from further clinical assay based on determining the concentration of at least one interferent in the sample, the method comprising the steps of:
   positioning the sample container in a spectrophotometer such that the sample can be irradiated by the spectrophotometer;
   irradiating the sample with at least one frequency of radiation;
   correlating absorbance of the radiation by the sample with a standard for the interferent(s) to determine the concentration of the interferent(s); and
   rejecting the sample if the concentration of the interferent(s) exceeds a predetermined criteria.

2. The method as claimed in claim 1 wherein the radiation is near infrared and adjacent visible region light.

3. The method as claimed in claim 2 wherein said near infrared and adjacent visible region light has wavelengths from about 450 nm to about 1080 nm.

4. The method as claimed in claim 3 where the interferent is selected from the group consisting of haemoglobin, bilirubin, and intralipid.

5. The method as claimed in claim 4 wherein the frequencies of radiation are 603 nm, 679 nm and 1044 nm all of which are used to correlate to quantities of haemoglobin; 641 nm, 662 nm, 731 nm, and 763 nm all of which are used to correlate to quantities of bilirubin; and 975 nm which is used to correlate to quantities of intralipids.

6. The method of claim 5, wherein said correlating includes calculating the first derivatives of at least two portions of a spectrum generated from a scan for a particular interferent which are used in an algorithm in respect of the interferent(s) to calculate the particular interferent(s) concentration(s).

7. The method of claim 6, wherein integration time for said sample beam is low for clear samples and automatically switched to a higher integration time for turbid samples.

8. The method as claimed in claim 1 wherein said sample includes a label, a container and a specimen and said radiation is transmitted through said label which is located on the exterior of said container.

9. A method for rejecting a plasma sample contained in a sample container from further clinical assay based on determining the concentration of at least one interferent in the sample, the method comprising the steps of:
   positioning the sample container in a spectrophotometer such that the plasma sample can be irradiated by the spectrophotometer;
   irradiating the plasma sample with at least one frequency of radiation;
   correlating absorbance of the radiation by the plasma sample with a standard for the interferent(s) to determine the concentration of the interferent(s) including calculating the first derivatives of at least two portions of a spectrum generated from a scan for a particular interferent which are used in an algorithm in respect of the interferent(s) to calculate the particular interferent(s) concentration(s); and
   said algorithm(s) in respect of haemoglobin, bilirubin and intralipids are, respectively:

$ln[(g/L \text{ haemoglobin})+1]=7.58(603 \text{ nm})+11.75(679 \text{ nm})21.50(1,044 \text{ nm})+0.31$  a.

where (Xnm) is the first derivative of the value of an absorbance measured at the wavelength specified;

$\mu moles/L \text{ bilirubin}=-3601(641 \text{ nm})+3415(662 \text{ nm})+12710(731 \text{ nm})-8214(763 \text{ nm})-120$  b.

where (Ynm) is the first derivative of the value of an absorbance measured at the wavelength specified; and $ln(g/L \text{ intralipids})=1.53(975 \text{ nm})-8.48$  c.

where (Znm) is the raw absorbance measured at the wavelength specified; and rejecting the plasma sample if the concentration of the interferent(s) exceeds a predetermined criteria.

10. The method as claimed in claim 9 wherein said algorithms in respect of haemoglobin, bilirubin, and intralipid are, respectively:

Haemoglobin $g/L Hb=24.14(591 \text{ nm})-23.64(617)-0.93$

Bilirubin $mg/dL \text{ Biii}=142.09(511 \text{ nm})+89 g(554 \text{ nm})-4.47$

Intralipid $g/L IL=44.91(992 \text{ nm})+222.24(1044 \text{ nm})-0.98$

Where (Xnm) is the first derivative of the absorbance measurement at the wavelengths specified for all three interferents.

11. A method for rejecting a sample contained in a sample container from further clinical assay based on determining the concentration of at least one interferent in the sample, the method comprising the steps of:

positioning the sample container in a spectrophotometer such that the sample can be irradiated by the spectrophotometer;

irradiating the sample with at least one frequency of radiation;

correlating reflectance of the radiation by the sample with a standard for the interferent(s) to determine the concentration of the interferent(s); and rejecting the sample if the concentration of the interferent(s) exceeds a predetermined criteria.

12. The method as claimed in claim 11 wherein the radiation is near infrared and adjacent visible region light.

13. The method as claimed in claim 12 wherein said near infrared and adjacent visible region light has wavelengths from about 450 nm to about 1080 nm.

14. The method as claimed in claim 13 where the interferent is selected from the group consisting of haemoglobin, bilirubin, and intralipid.

15. The method of claim 11 wherein the first derivative of absorbance is used to correlate said quantity of interferent.

\* \* \* \* \*